United States Patent
Ashton et al.

[11] Patent Number: 5,836,935
[45] Date of Patent: Nov. 17, 1998

[54] IMPLANTABLE REFILLABLE CONTROLLED RELEASE DEVICE TO DELIVER DRUGS DIRECTLY TO AN INTERNAL PORTION OF THE BODY

[76] Inventors: Paul Ashton, 75 Chestnut St., #13, Boston, Mass. 02108; Roy A. Patchell, 442 Fayette Park, Lexington, Ky. 40508; Jon Cooper, P.O. Box 55552, Lexington, Ky. 40555; Byron A. Young, 2040 Von List Way, Lexington, Ky. 40502

[21] Appl. No.: 789,242

[22] Filed: Jan. 28, 1997

Related U.S. Application Data

[63] Continuation of Ser. No. 339,246, Nov. 10, 1994, abandoned.

[51] Int. Cl.⁶ ................................................. A61N 1/30
[52] U.S. Cl. ................... 604/891.1; 604/246; 604/890.1; 424/424
[58] Field of Search ..................... 604/246, 247, 604/252, 891.1, 890.1, 892.1, 8, 9; 424/422–424, 449

[56] References Cited

U.S. PATENT DOCUMENTS

| | | | |
|---|---|---|---|
| 3,310,051 | 3/1967 | Schulte | 128/216 |
| 3,894,538 | 7/1975 | Richter | 604/890.1 |
| 4,273,761 | 6/1981 | Matsuda et al. | |
| 4,511,355 | 4/1985 | Franetzki et al. | |
| 4,568,331 | 2/1986 | Fischer et al. | |
| 4,588,394 | 5/1986 | Schulte et al. | 604/9 |
| 4,681,560 | 7/1987 | Schulte et aL. | 604/9 |
| 4,687,468 | 8/1987 | Gianturco | 604/9 |
| 4,761,158 | 8/1988 | Schulte et al. | 604/9 |
| 4,816,016 | 3/1989 | Schulte et al. | 604/9 |
| 4,857,053 | 8/1989 | Dalton | 604/93 |
| 4,871,352 | 10/1989 | Tran | 604/892.1 X |
| 4,969,871 | 11/1990 | Theeuwes et al. | |
| 5,011,472 | 4/1991 | Aebishcer et al. | 604/892.1 X |
| 5,041,107 | 8/1991 | Heil, Jr. | 604/891.1 |
| 5,051,257 | 9/1991 | Pietronigro | |
| 5,084,015 | 1/1992 | Moriuchi | 604/9 |
| 5,087,616 | 2/1992 | Myers et al. | |
| 5,116,493 | 5/1992 | Chick et al. | 424/424 |
| 5,160,320 | 11/1992 | Yum et al. | |
| 5,180,820 | 1/1993 | Barde et al. | |
| 5,229,500 | 7/1993 | Barde et al. | |
| 5,291,887 | 3/1994 | Stanley et al. | 604/289 |

OTHER PUBLICATIONS

Morantz, R.A. et al., "Bleomycin and Brain Tumors. A Review", J. Neurooncol. (US), 1983, pp. 249–255. (abstract only).

Nakazawa, S. et al., "New Management of Brain Neoplasms. Local Injection of Adriamycin", No Shinkei Geka (Japan), Aug. 1983, 11(8), pp. 821–827. (abstract only).

Nakazawa, S. et al., "A New Treatment of Malignant Brain Tumor–1: Local Injection of Bleomycin", No Shinkei Geka (Japan), Dec. 1981, 9(13), pp. 1487–1493. (abstract only).

Nakajima, F. et al., "A Case of Alpha–Fetoprotein Producing Primary Intracranial Embryonal Carcinoma Treated with Combination Chemotherapy with Cis–platinum, Vinblastine and Bleomycin", No Shinkei Geka (Japan), 1981, 9(3), pp. 371–375. (abstract only).

Shimura, T. et al., "Disseminated Necrotizing Leukoenecephalopathy Accompanied with Multiple Calcium Deposits Following Antineoplastic and Radiation Therapy in a Case of Intracranial Germ Cell Tumor: Computerized Tomographical Study", No Shinkei Geka (Japan), Jun. 1989, 17(6), pp. 573–577. (abstract only).

McKeran, R.O. et al., "A Potential Application for the Intracerebral Injection of Drugs Entrapped within Liposomes in the Treatment of Human Cerebral Gliomas", J. Neurol. Neurosurg. Psychiatry (England), Dec. 1985, 48 (12), pp. 1213–9 (abstract only).

*Primary Examiner*—Michael Powell Buiz
*Assistant Examiner*—Chalin Smith
*Attorney, Agent, or Firm*—Lowe, Price, LeBlanc & Becker

[57] ABSTRACT

An implantable, refillable, rate-controlled drug delivery device, with a hollow reservoir, and a drug delivery tube communicating with the hollow reservoir. The drug delivery tube includes at least one rate-limiting permeable membrane which regulates drug delivery. A method of controlling the delivery of a drug to an internal portion of a body is disclosed.

9 Claims, 4 Drawing Sheets

IMPLANTABLE REFILLABLE CONTROLLED RELEASE DEVICE TO DELIVER DRUGS DIRECTLY TO AN INTERNAL PORTION OF THE BODY

This application is a continuation of application Ser. No. 08/339,246 filed Nov. 10, 1994, now abandoned.

TECHNICAL FIELD

The present invention relates to an implantable, refillable, rate-controlled drug delivery device, with a hollow reservoir, and a drug delivery tube communicating with the hollow reservoir. The drug delivery tube includes at least one rate-limiting permeable membrane which regulates drug delivery. A method of controlling the delivery of a drug to an internal portion of a body is also disclosed.

BACKGROUND

Implantable devices for drug delivery are known. U.S. Pat. No. 3,310,051 to Schulte discloses a ventricular catheter with a reservoir, a backing member and a tube.

U.S. Pat. No. 5,511,355 to Franetzki et al. discloses an infusion device intended for implantation into the human body. The device comprises a flexible walled reservoir in a housing to contain the infusion liquid; a dosing unit for conveying the infusion liquid from the housing to a catheter, means permitting the refilling of the reservoir. The device is useful for delivering insulin.

U.S. Pat. No. 4,969,871 to Theeuwes et al. discloses a drug delivery device comprising a reservoir containing a beneficial agent to be delivered. The delivery device includes a drip chamber attached to tubing which is further attached to a transdermal delivery device. The tubing may have attached a formulator which includes a flow distributor. The delivery device is a transdermal drug delivery device comprising a reservoir attached to the skin by an adhesive.

U.S. Pat. No. 4,568,331 to Fischer et al. discloses a disposable medicine dispensing device. The device comprises a dispenser with walls which define a chamber which holds a medicament; a removable cap for refilling the reservoir; a delivery tube and a valve means for controlling delivery of the solution through the tube.

Heyer Shulte Medical Catalog discloses an Ommaya reservoir with either an on-off flushing device, or with a pressure pump to regulate brain pressure. Codman Medical Catalog discloses an Ommaya reservoir with a pressure flow control. P.S. Medical Catalog discloses an Ommaya reservoir with a pressure flow control.

"Osmet" by Alza is a pump which works by osmotic pressure, and polyanhydride matrices by Nova. Polyanhydrides are bioerodible polymers and this system uses matrices of drug (BCNU) in a polyanhydride base. The processes involved in release are dissolution of BCNU, diffusion through the matrix and breakdown of the polyanhydride. These systems work by a different mechanism to that reported here.

Drugs for the treatment of tumors are known. For example, U.S. Pat. No. 5,087,616 to Meyers et al. discloses cytotoxic drug conjugates and their delivery to tumor cells. The cytotoxic substances include daunomycin, bleomycin, melphalan, chlorambucil, cysplatin, vinblastine, vincristine, or anti-metabolites such as methotrexate.

U.S. Pat. No. 5,051,257 to Pietronigro discloses anti-neoplastic solutions for direct intra-tumoral delivery. The anti-neoplastic agents include nitrosourea, preferably BCNU. (1,3-bis(2-chloroethyl)-1-nitrosourea). The compound may be needle injected into brain tumors.

U.S. Pat. No. 4,273,761 to Matsuda et al. discloses an anti-tumor composition containing bleomycin and an absorption enhancer for the treatment of a gastro-intestinal tumor site. The drug is administered orally or through subcutaneous injection.

U.S. Pat. No. 5,229,500 to Barde et al. discloses a brain derived neurotrophic factor (or BDNF) which can be delivered via an Ommaya reservoir (see column 35, lines 33–35).

U.S. Pat. No. 5,180,820 to Barde et al. discloses antibodies directed toward brain derived neurotrophic factor which can be delivered via an ommaya reservoir.

R.A. Morantz et al., "Bleomycin and brain tumors. A review." J. Neurooncol. (United States), 1983, pp. 249–55. This publication discloses the delivery of bleomycin to brain tumors using an Ommaya reservoir.

S. Nakazawa et al., "New management of brain neoplasms. 2. Local injection of adriamycin." No Shinkei Geka (Japan), August 1983, 11 (8), pp. 821–7. This publication discloses the delivery of bleomycin to brain tumors using an Ommaya reservoir.

S. Nakazawa et al., "A new treatment of malignant brain tumor −1: local injection of bleomycin." No Shinkei Geka (Japan), December 1981, 9 (13), pp. 1487–93. This publication discloses the delivery of bleomycin to brain tumors using an Ommaya reservoir which is implanted subcutaneously under the scalp.

F. Nakajima et al., "A case of alpha-fetoprotein producing primary intracranial embryonal carcinoma treated with combination chemotherapy with cis-platinum, vinblastine and bleomycin." No Shinkei Geka (Japan), 1981, 9 (3), pp. 371–5. This publication discloses the delivery of bleomycin to brain tumors using an Ommaya reservoir.

T. Shimura et al., "Disseminated necrotizing leukoencephalopathy accompanied with multiple calcium deposits following antineoplastic and radiation therapy in a case of intracranial germ cell tumor: Computerized tomographical study." No Shinkei Geka (Japan), June 1989, 17 (6), pp. 573–7. This publication discloses the intraventricular delivery of bleomycin to brain tumors using an Ommaya reservoir.

R.O. McKeran et al., "A potential application for the intracerebral injection of drugs entrapped within liposomes in the treatment of human cerebral gliomas." J. Neurol. Neurosurg. Psychiatry (England), December 1985, 48 (12), pp. 1213–9. The publication discloses the delivery of bleomycin to brain tumors using an Ommaya reservoir.

Known devices may include pressure releasing valves to release or regulate pressure in the brain or drain fluid from the brain. No rate-limiting permeable membrane designed to release the drug to be delivered at a controlled rate or means for controlling drug delivery is present in existing implantable drug delivery devices.

The present device overcomes the deficiencies of the prior art by providing an implantable, refillable, drug delivery device with a means for controlling drug delivery with at least one rate-limiting permeable membrane.

DISCLOSURE OF THE INVENTION

It is an object of this invention to provide a device which, once implanted, gives continuous access to internal regions of the body without requiring additional needle penetrations into these regions. Instead, a tubular portion of the device remains in the body and extends to the affected area where it serves as a continuously-available conduit placed there but once. Thereafter, a syringe or other device need only be placed in fluid communication with this conduit to inject, withdraw or mix fluids in the interior region. The delivery tube is equipped with at least one rate-limiting permeable membrane designed to release the drug to be delivered at a controlled rate.

In a preferred embodiment the device is adapted to deliver a drug to a brain tumor at a controlled rate.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

Figure 1:
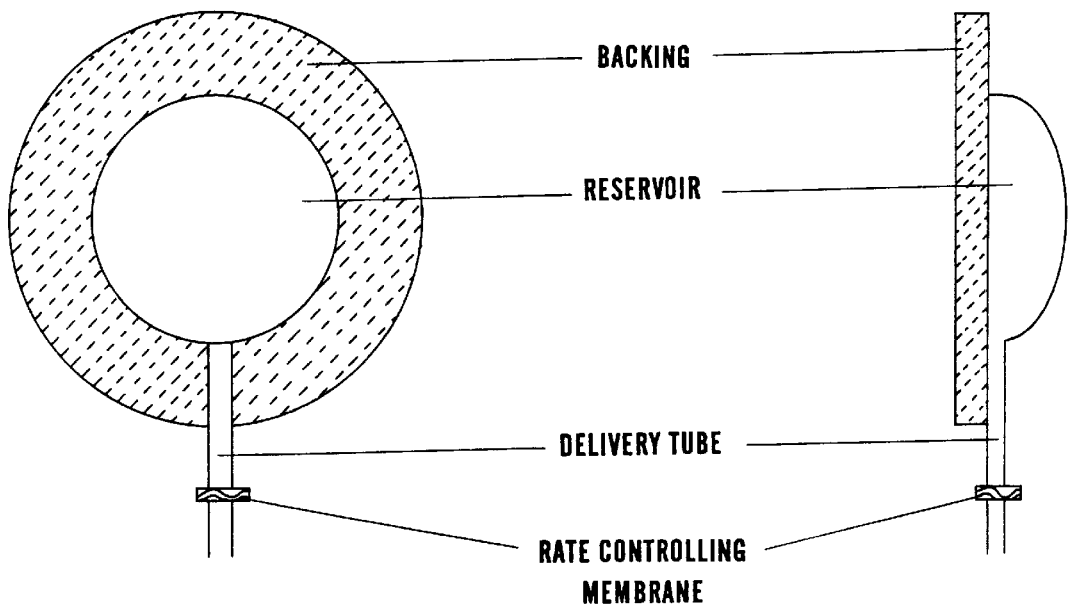
FIG. 1 shows a schematic of the control delivery device of the present invention.

This invention provides a device which, once implanted, gives continuous access to internal regions of the body without requiring additional needle penetrations into these regions. Instead, a tubular portion of the device remains in the body and extends to the affected area where it serves as a continuously-available conduit placed there but once. Thereafter, a syringe or other device need only be placed in fluid communication with this conduit to inject, withdraw or mix fluids in the interior reservoir. The device has a rate-limiting permeable membrane designed to release the drug to be delivered at a controlled rate. In a preferred embodiment the device further comprises a backing member, such as a membrane, circumscribing the hollow reservoir.

In a more preferred embodiment, the device is designed to deliver a drug to a brain tumor at a controlled rate. The apparatus of the invention is composed of a refill-able reservoir containing a drug solution connected to a delivery tube. The tube is inserted into the target region of the brain (tumor) through a hole drilled in the skull. The reservoir remains outside the skull under the scalp so it can be easily refilled. Diffusion of drug from the reservoir into the tube and hence the brain is controlled by a rate-limiting permeable membrane. The rate of delivery into the brain is controlled by the membrane and by the drug concentration in the reservoir.

This device enables a large variety of drugs and other agents to be delivered into any internal region of the body, preferably the brain. Bleomycin is a preferred drug used in the reservoir delivery device for the treatment of brain tumors.

Brain tumors are the second leading cause of death from cancer in pediatrics and the fourth leading cause among middle aged men. Each year in the United States approximately 40,000 people are diagnosed with a primary brain tumor or secondary brain malignancy (1) [see References below] and 10,000 die (2). Glioblastoma is particularly devastating. Despite aggressive multimodal therapy the 2 year survival rate is approximately 25% (3) and new treatment modalities are urgently needed.

In the brain cellular proliferation is normally extremely limited so it could be expected that brain tumors would be susceptible to cell cycle specific agents. There are however, two major problems which limit the usefulness of chemotherapy. Firstly, although high levels of drugs can be achieved in the blood many drugs penetrate the blood brain barrier poorly and so fail to achieve therapeutic levels in the target area. This is especially true for hydrophilic drugs (4,5). The second problem is that in glioblastomas ts the cells involved with grow slowly (although much faster than healthy brain tissue). Usually less than 10% of the cells in a brain tumor are actively cycling at any one time (2).

The most direct route of administration to brain tumors is direct intratumoral (IT) injection. An advantage of this route is that most primary brain tumors and metastases are localized in a single region so IT injection can localize, at least initially, delivery to the target area. Human and animal studies with IT delivery of antibiotics such as adriamycin (6) and lomustine, (7) have demonstrated high concentrations of drug in the brain and, in some cases, increased survival times (6).

In human studies, IT administration is normally performed with an indwelling catheter implanted into the brain and linked to a refillable reservoir under the scalp (8). Despite the use of a variety of cytotoxic agents clinical results have been disappointing (8–10). The slow growth rate of brain tumors suggests that better results would be obtained if therapeutic concentrations of cytotoxic agents, especially cell cycle specific ones, could be maintained for a prolonged period.

Bleomycins are a group of large (molecular weight 1400) hydrophilic compounds isolated from streptomyces verticillus. Bleomycins are believed to interact with DNA and cause strand scission, a review of the mode of action is given by Byrnes et al., 1990 (11). Bleomycin causes an accumulation of cells in the G2 phase in vitro (12) and are used in a variety of tumors including squamous carcinomas of the skin, neck and lungs in addition to lymphomas and testicular tumors (12). Bleomycin localizes on and within tumor cells (13) and has a special affinity for ectodermal tissues (14). Bleomycin has been shown to inhibit the growth of human glioma cells in culture at a concentration of over 0.47 $\mu$M (15). As gliomas are ectodermal in origin, bleomycin could be expected to be effective against these tumors. Bleomycin is preferentially taken up by malignant brain tissue and $^{57}$Co labelled bleomycin scintigraphy can be used to detect brain metastases (16).

EXAMPLE 1

Materials and methods

Polyvinyl alcohol, 98% hydrolyzed, was purchased from Aldrich Chemical Co. The molecular weight range was 70–80k. Bleomycin sulphate (Blenoxane) was obtained from Nippon Kayaku Co. Ltd. of Japan. Sodium phosphate (mono and di basic was purchased from Fisher Scientific).

Release of Bleomycin from Implantable, Rate Controlled Drug Delivery Reservoir

Solutions of polyvinyl alcohol (PVA) were prepared by dissolving 2 g of PVA in 100 ml of deionized water at 80° C. After cooling to room temperature the solution was poured onto a glass plate and allowed to dry forming a thin film. The film was then removed and heated to 120° C. for 2 hours. 1 $cm^2$ pieces of the film were cut and fixed (FIG. 1). The hollow reservoirs were filled with phosphate buffer (pH 7.4) containing 3 U/mL bleomycin and the delivery tubes immersed in 5 mL buffer. Care was taken to ensure that no air bubbles were trapped in the reservoir, tube or connector. Samples (1 mL) were periodically removed and assayed by uv detection at 290 nm.

After 10 days the bleomycin solution was removed from the reservoir with a 5 ml syringe and a 20 gauge needle. The reservoir was then refilled with a 10 U/mL bleomycin solution and the release again measured for 10 days. The same process was repeated once more with a 22.5 U/ml bleomycin solution.

Implantation into the Rat Brain

Animals were anesthetized by subcutaneous injection of 0.4 ml of a ketamine/rompun mixture (55%:45%). The skull was then exposed with a #11 scalpel and a 3 mm hole drilled through the skull to expose the dura. The tip of the tube was then inserted through the dura to a depth of 3 mm. The tube was then fixed in place with dental acrylic and the wound closed with silk suture. The reservoir was then filled with a 3 U/ml bleomycin solution. An incision was then made in the rat's back and the reservoir implanted under the skin.

Release of Bleomycin from Reservoir

Figure 2:
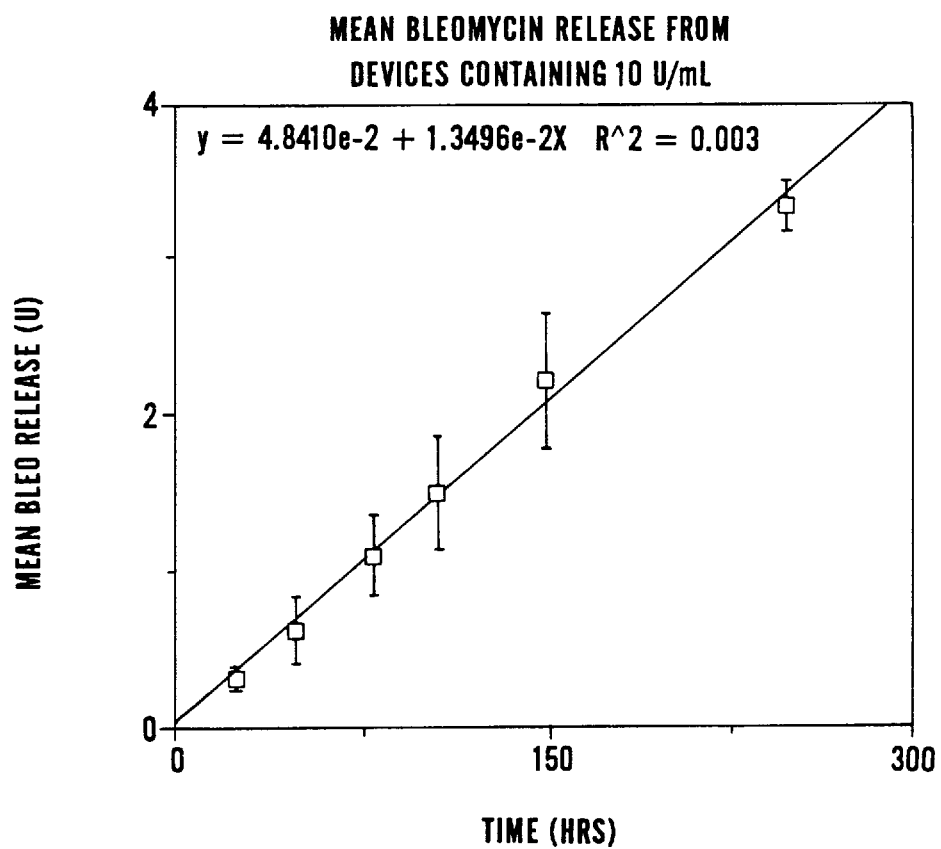
FIG. 2 shows release of bleomycin from the reservoirs was pseudo zero order for the first 7 days. This corresponds to approximately 25% bleomycin release. After this time release began to slow reflecting depletion of the reservoir. Refilling the tubes repeatedly did not appear to affect the percentage release per unit time.
Figure 3:
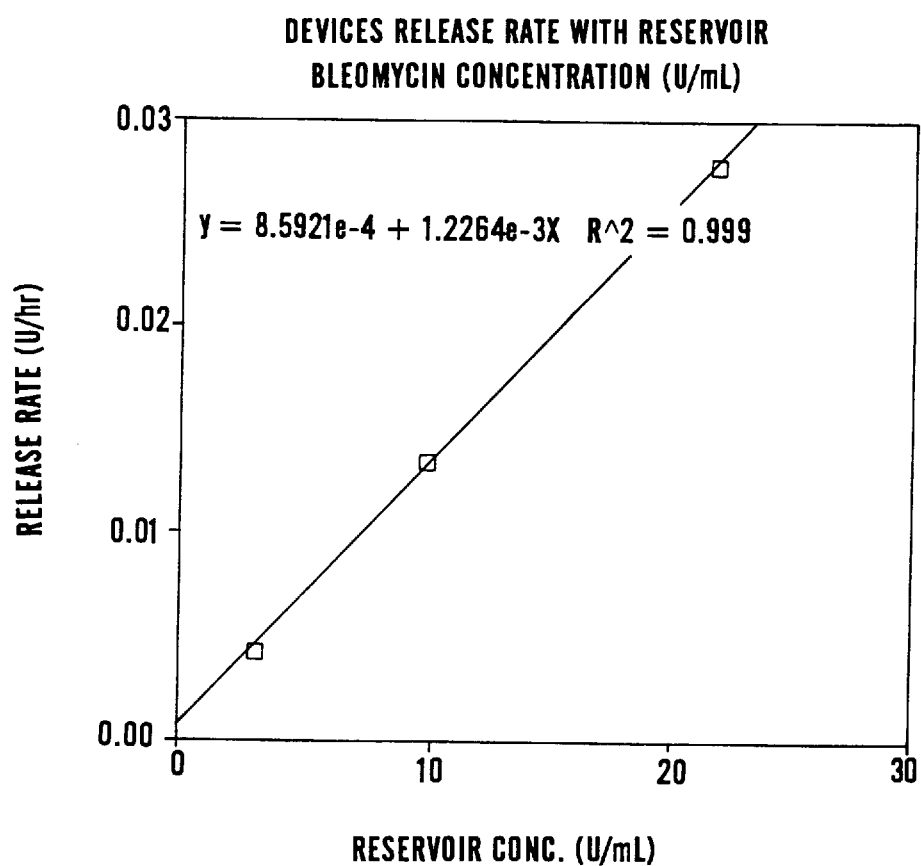
FIG. 3 shows the release rate over the first 7 days after refilling was found to be directly proportional to the concentration of bleomycin in the reservoir

Release of bleomycin from the reservoirs was pseudo zero order for the first 7 days (FIG. 2). This corresponds to approximately 25% bleomycin release. After this time release began to slow reflecting depletion of the reservoir. Refilling the tubes repeatedly did not appear to affect the percentage release per unit time and the release rate over the first 7 days after refilling was found to be directly proportional to the concentration of bleomycin in the reservoir (FIG. 3).

Implantation into the Rat Brain

Animals appeared to fully recover after implantation with no observable loss of mobility or motility. The in vitro data shows that release from the devices is pseudo-zero order and is directly proportional to the concentration in the reservoir. The data also shows that the devices can be refilled without changing the release properties. Previous work has shown that direct intracranial infusions of bleomycin can be tolerated in rats and humans (18). Similarly devices of PVA have been implanted into a variety of sites in the body with no ill effects (19,20) and implantable reservoirs are well tolerated. The work presented here shows that implantable reservoirs containing bleomycin and a membrane of PVA are well tolerated.

A device according to this invention comprises a tube having a central passage, the tube being adapted to be inserted in to an internal portion of the body so that its passage communicates with a selected region therein. A hollow reservoir is adapted to be connected to this tube and to be placed beneath the skin of the body. This hollow reservoir comprises an enclosure which has an internal periphery and a first and second wall, these walls facing each other inside the reservoir. The wall next to the skin is tolerant to, and self-sealing after, needle puncture. One of the walls has a passage through the tube. The tube is adapted to include a rate-limiting permeable membrane to control the rate of drug delivery to the target area. In a preferred embodiment the delivery tube comprises two rate-limiting permeable membranes.

Thus, the invention relates to an implantable, refillable reservoir containing a drug solution connected to a delivery tube. The tube is inserted into an internal target region of the body. Diffusion of the drug from the reservoir into the tube and into the target area of the body is controlled by a rate-limiting permeable membrane. The rate of delivery into the target area of the body is controlled by the membrane and by the drug concentration in the reservoir.

According to a preferred but optional feature of the invention, one of the walls is flexible and palpable through the skin by force exerted by the hand. The material of the flexible wall is flexible enough to be moved toward the other wall and thereby reduce the volume of the reservoir, and also sufficiently springy to return to its normal unstressed condition, thereby providing for pumping means to create bi-directional flow in the passages for mixing purposes.

Figure 4:
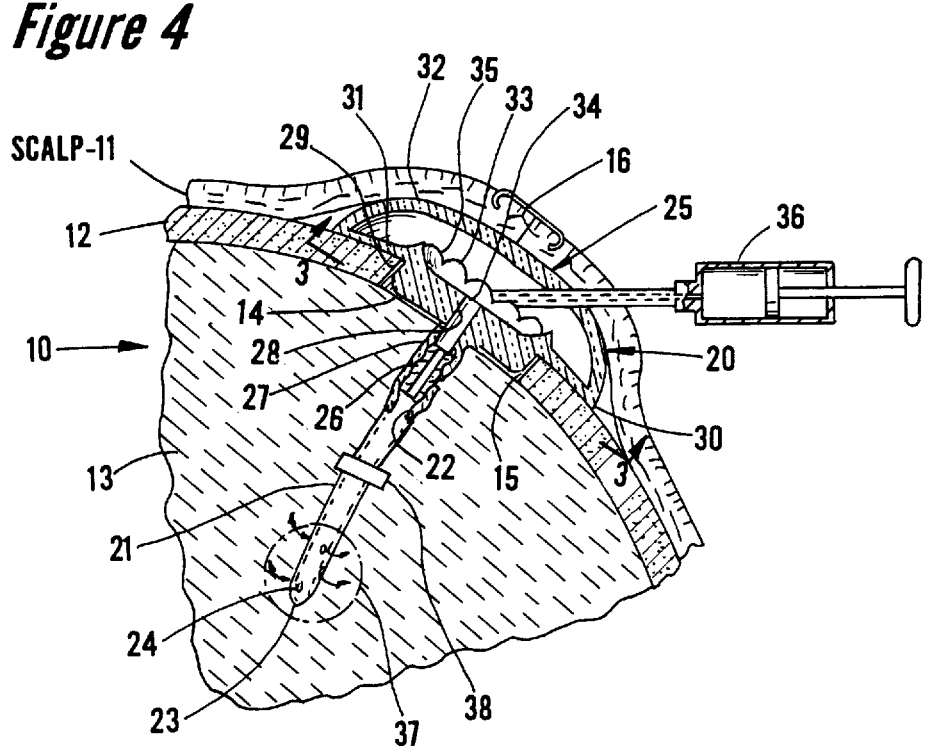
FIG. 4 is a cross-section of a portion of a skull, showing the device of the invention, partly in cutaway cross-section and in its normal, unstressed condition.
Figure 5:
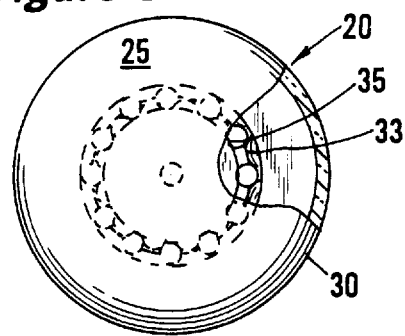
FIG. 5 is a top view of the invention, partly in cutaway cross-section.
Figure 6:
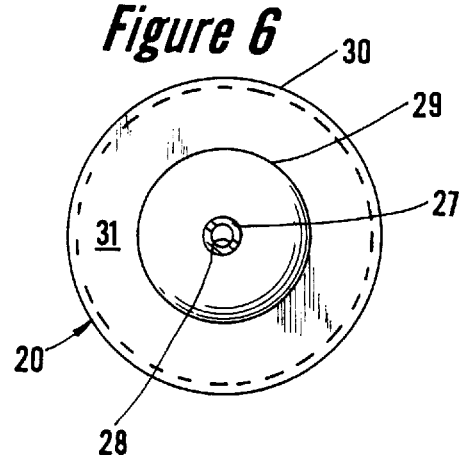
FIG. 6 is a bottom view of the device taken at line 3—3 of FIG. 4.

The above and other features of this invention will be fully understood from the following detailed description and the accompanying drawings in which:

FIG. 4 illustrates a skull 10, showing the scalp 11 and the bone 12 of the skull surrounding the brain 13. The drawing of the anatomical portions is simplified because these form no portion of the present invention. It will be noted that the device is installed within a burr hole 14 having an internal wall 15 in the bone of the skull, and is held beneath the skin of the scalp by means of a sutured slit 16.

The reservoir, elements 20 comprising the invention includes a tube 21 having a central passage 22 and a closed end 23. Perforations 24 through the wall provide for fluid communication between the passage and the outside of the tube. The tube is connected to a reservoir 25 by means of a connector 26, which connector is attached to a passage extension 27 which has a passage 28 that enters the reservoir itself through one wall thereof. The tube is equipped with at least one rate-limiting permeable membrane 38 for controlling the rate of drug delivery to the target area of drug delivery. In an alternative embodiment the rate-limiting permeable membrane may be place in any location in the tube or between the opening of the reservoir and the tube. The reservoir has a boss 29 which fits within burr hole 14 and provides for lateral restraint of the device. The reservoir outward of the boss rests on the skull so as to give longitudinal restraint.

The reservoir is a continuous enclosure and includes a circumferential periphery defined by circumferential edge 30. First and second interior walls 31, 32 are provided on opposite sides of the periphery. The first wall lies closer to the skull, and includes an interior crown 33 which surrounds the opening 34 of passage 28 into the interior of the reservoir. The crown has a plurality of notches 35 formed therein.

Second wall 32 is generally domed and has a central section which is thicker than the edges. This wall is flexible and, as best shown in FIG. 4, is adapted to be palpated by finger pressure through the scalp to move it toward the first wall, thereby reducing the volume of the reservoir. In order to prevent the first and second walls from adhering to each other and closing the passages, the crown is provided to hold them apart. However, the notches provide for fluid flow past the crown to the passage even when the second wall is pressed against the crown.

The entire structure is made of material which is compatible with the human tissue with which it comes in contact. A convenient substance is silicone rubber manufactured by Dow Corning Company, of Midland, Michigan. In a preferred embodiment the material of the device is polyvinyl alcohol. If a backing member is present in a preferred embodiment, the backing member may be composed of any material tolerated by the human body, preferably ethylene vinyl acetate, Teflon, silicone, silastic and nylon. The rate-limiting permeable membrane may be composed of a composition such as polyvinyl alcohol, ethylene vinyl acetate, silicone, nylon, polypropylene, polcarbonate, cellulose, cellulose acetate, cellulose esters or polyether sulfone.

Figure 7:
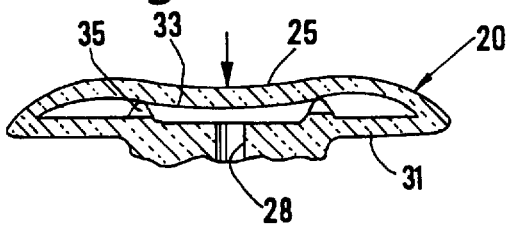
FIG. 7 is a fragmentary cross-section of a portion of FIG. 4, showing the device in another of its conditions.

The thickness of the second wall is selected such that it is springy enough to restore itself to its normal, unstressed condition shown in FIG. 4, and yet sufficiently flexible that it can be deflected to the configuration shown in FIG. 7. It is also tolerant to repetitive needle punctures (with a reasonable number), because, as best shown in FIG. 4, material may be injected from a hypodermic syringe 36 by puncturing the scalp and the second wall with the needle. When the needle is withdrawn, the material of the second wall will seal the opening made by the needle.

The use of the device should be evident from the foregoing. The device may be used to control the rate of drug delivery to any internal region of the body.

In a most preferred embodiment the device is adapted for only drug delivery. In an alternative embodiment, if it is desired either to withdraw fluid from region 37 within the brain or to introduce medication thereto, the tube will be forced into this region by means well known in the surgical arts. Once in place, this tube is connected to the reservoir, and the reservoir is placed in position as shown, and the scalp sutured over the reservoir. Medication may be introduced to the region by a syringe as shown, mixing being attained either by depressing the second wall or by pumping with the syringe.

It will thereby be seen that this device provides a reservoir of fluid which in effect is an extension of a region under treatment or study. Only one puncture of the brain or other region is necessary because the tube remains in place for sensible periods of time to provide a continuously-available conduit to the region, and the dome is available for introduction and withdrawal, of material even were the second wall to be too stiff to flex. On the other hand, should the device be made flexible enough for this purpose, then even better results may be attained as a result of the more complete bi-directional flow attainable thereby.

EXAMPLE 2

A phase I trial of IT bleomycin for recurrent malignant gliomas was completed using the implantable reservoir according to the present invention. See University of Kentucky IRB #93–30026, incorporated herein by reference in its entirety. The device was extremely well tolerated. Nine patients were enrolled in a dose escalation study and received weekly doses of bleomycin beginning at 4.9 units per week and escalating to 24.5 units per week. The study determined that the maximum tolerable weekly doses of intratumoral bleomycin is 16 units per week. Toxicity, when present, was minimal at even higher doses and, when present, consisted of drowsiness, lethargy and increased seizure frequency in those patients with existing seizure disorders. Two patients who received cumulative doses of 300 units developed skin ulcers around the injection sites. No other neurological or systemic toxicity from bleomycin occurred. The median survival after start of IT bleomycin therapy was 39 weeks, and this compares favorably with the 8–12 week expected survival with patients with recurrent high grade gliomas. The phase I study showed that the implantable reservoir of the invention worked well without adverse effects and that IT dose of bleomycin was relatively non-toxic and well tolerated.

In sum, the invention provides an implantable, refillable reservoir containing a drug solution connected to a delivery tube. The tube is inserted into a specific target region of the body or may be placed in a region such as a blood vessel, to provide systemic distribution of the drug.

Diffusion of the drug from the reservoir into the tube and into the target area of the body is controlled by at least one rate-limiting permeable membrane. The rate of delivery into the target area of the body is controlled by the membrane and by the drug concentration in the reservoir.

REFERENCES

1. Rutka, J.T., Trent, J.M. and Rosenblum, M.L. Cancer Invest. 8:425–438 (1990).
2. Saleman, M. Neurologic Clinics 3,2:229–257 (1985.
3. Saleman, M., Kaplan, R.S., Ducker, T.B. et al. Neurosurgery 10:44–463 (1982).
4. Chen, H.-S.G. and Gross, J.F. Cancer Treat. Rep., 64:31–40 (1980).
5. Stewart, D.J., Prog. Exp. Tumor Res. 28:32–50 (1984).
6. Shimura, T. and Nakazawa, S. No Shinkei Geka. 8:35–42 (1980).
7. Tator, C.H. Surg. Neurol. 7:73–77 (1977).
8. Ringkjob, R. Acta. Neurol. Scand. 44:318–322 (1968).
9. Weiss, S.R. and Radkind, R. Internat. Surg. 31:149–155 (1969).
10. Newton, W.A., Sayers, M.P. and Samuels, L. Cancer Chemother. Rep. 52:52:257–261 (1968).
11. Byrnes, R.W., Templin, J., Sem D., Lyman, S. and Petering, D.H. Cancer Res. 50:5275–5286 (1990).
12. Goodman and Gilman's The Pharmacological Basis of Therapeutics Eds. A. G. Gilman, T. W. Rail, A. S. Nies and P. Taylor. Pergamon Press, 1990, 8th Ed.
13. Fujimoto, J. Cancer Res. 34:2969 (1974).
14. Blum, R.H., Carter, S.K. and Agre, K. Cancer. 31:903 (1973).
15. Kanno, T., Kudo, T. and Nakazawa, T. Clin. Neurol. 10:409–414 (1970).
16. Nieweg, O., Piers, D.A. and Beekhuis, H. Clin. Neurol. Neurosurg. 90–92, 109–111 (1988).
17. Adamson, I.Y.R., and Bowden, D.H. Am. J. Path. 77:185 (1975).
18. Morantz, R.A., Kimler, B.F., Vats, T.S. and Henderson, S.D. J. Neuro. Oncol. 1:249–255 (1983).
19. Sanborn, G.E., Anand, R., Tori, R.E., Nightingale, S.D., Cal, S.X., Yates, B., Ashton, P. and Smith, T.J. Arch. Ophthalmol. 110:188–195 (1992).
20. Blandford, D.L., Smith, T.J., Brown, J.D., Pearson, P.A. and Ashton, P. Invest. Ophthalmol. Vis. Sci. In press.

The purpose of the above description and examples is to illustrate some embodiments of the present invention without implying any limitation. It will be apparent to those of skill in the art that various modifications and variations may be made to the apparatus and method of the present invention without departing from the spirit or scope of the invention. All patents and publications cited herein are incorporated by reference in their entireties.

We claim:

1. An implantable, refillable, rate controlled drug delivery device, comprising a hollow reservoir, a drug delivery tube communicating with the hollow reservoir, and one or more rate-limiting elements, said one or more elements consisting essentially of a permeable membrane in said drug delivery tube, which membrane passively regulates drug delivery.

2. The device according to claim 1, wherein said device comprises two rate-limiting permeable membranes.

3. The device according to claim 1 wherein said rate-limiting permeable membrane is located between the hollow reservoir and an opening of the drug delivery tube.

4. The device according to claim 1, wherein said hollow reservoir contains a drug to be delivered at a controlled rate to an eternal target area of the body.

5. The device according to claim 4, wherein said internal target area of the body is the brain.

6. The device according to claim 1, further comprising a backing member circumscribing the hollow reservoir.

7. The device according to claim 6, wherein said backing member is a membrane.

8. A method of controlling the delivery of a anti-tumor drug to an internal portion of a body comprising administering an anti-tumor drug to an internal portion of the body through a device according to claim 1 to control the delivery of the anti-tumor drug.

9. A method for treating a brain tumor comprising administering an anti-tumor drug to a brain tumor through a device according to claim 1 to regulate drug delivery to the brain tumor.

* * * * *